(12) United States Patent
O'Hara

(10) Patent No.: US 11,364,178 B2
(45) Date of Patent: Jun. 21, 2022

(54) GASTRIC TUBE STABILIZER

(71) Applicant: Thomas O'Hara, Ozark, MO (US)

(72) Inventor: Thomas O'Hara, Ozark, MO (US)

(*) Notice: Subject to any disclaimer, the term of this patent is extended or adjusted under 35 U.S.C. 154(b) by 318 days.

(21) Appl. No.: 16/801,036

(22) Filed: Feb. 25, 2020

(65) Prior Publication Data
US 2021/0259925 A1    Aug. 26, 2021

(51) Int. Cl.
| | |
|---|---|
| *F16M 11/00* | (2006.01) |
| *A61J 9/06* | (2006.01) |
| *A61J 15/00* | (2006.01) |
| *F16M 11/06* | (2006.01) |
| *F16M 13/02* | (2006.01) |
| *A61J 1/16* | (2006.01) |

(52) U.S. Cl.
CPC .......... *A61J 9/0638* (2015.05); *A61J 9/0676* (2015.05); *A61J 15/0026* (2013.01); *A61J 15/0061* (2013.01); *F16M 11/06* (2013.01); *F16M 13/022* (2013.01); *A61J 1/16* (2013.01); *A61M 2209/088* (2013.01)

(58) Field of Classification Search
CPC ....... F16M 11/06; A61J 9/0638; A61J 9/0676; A61J 15/0026; A61J 15/0061; A61M 5/1417
See application file for complete search history.

(56) References Cited

U.S. PATENT DOCUMENTS

| | | | | |
|---|---|---|---|---|
| 3,547,322 | A * | 12/1970 | Dawson | A61M 5/1415 604/179 |
| 4,120,304 | A * | 10/1978 | Moor | A61M 25/02 128/DIG. 26 |
| 4,504,267 | A * | 3/1985 | Parmelee | A61M 5/148 604/174 |
| 4,578,062 | A * | 3/1986 | Schneider | A41D 13/1245 604/174 |
| 6,280,422 | B1 * | 8/2001 | Sanchez-Browning | A61M 5/16877 215/11.4 |
| 6,899,102 | B1 * | 5/2005 | McGlothen | A61M 16/0666 128/207.18 |
| 2004/0262463 | A1 * | 12/2004 | Jackson | F16L 3/003 248/121 |
| 2008/0319397 | A1 * | 12/2008 | Macaluso | A61J 15/0061 604/174 |
| 2010/0325772 | A1 * | 12/2010 | Fladl | A41D 13/129 2/102 |

(Continued)

*Primary Examiner* — Amy J. Sterling
(74) *Attorney, Agent, or Firm* — Lyman Moulton, Esq.; Moulton Patents, PLLC

(57) ABSTRACT

The disclosure includes a device made of a lightweight plastic that will hook around the neck like a hanger, releasing with very little force to prevent injury. The device hangs down the front of the body to form a loop for stability. Down the center will be a retractable feeding tube holder arm that can adjust 180 degrees up and down and left to right, and lock-in any position in-between on a universal joint. The arm also will have a quick release to avoid injury. The arm will have an alternating clip to attach to variable size tubes as needed. This will allow for everyday support and hands free interaction with the tube. A pair of support arms terminate in a support pad each and attach to the universal joint. A method of supporting a gastric tube on a patient via the device is also disclosed.

20 Claims, 4 Drawing Sheets

(56) References Cited

U.S. PATENT DOCUMENTS

| | | | | |
|---|---|---|---|---|
| 2013/0338642 A1* | 12/2013 | Maulin | ............... | A61J 15/0026 |
| | | | | 604/533 |
| 2016/0263310 A1* | 9/2016 | Helbig | ................ | A61M 5/1415 |
| 2020/0030191 A1* | 1/2020 | Santillan | ................ | F16B 2/005 |

* cited by examiner

GASTRIC TUBE STABILIZER

BACKGROUND OF THE INVENTION

A feeding tube is a medical device used to provide nutrition to people who cannot obtain nutrition by mouth, are unable to swallow safely, or need nutritional supplementation. The state of being fed by a feeding tube is called gavage, enteral feeding or tube feeding. Placement may be temporary for the treatment of acute conditions or lifelong in the case of chronic disabilities. A variety of feeding tubes are used in medical practice. They are usually made of polyurethane or silicone. The diameter of a feeding tube is measured in French units (each French unit equals ½ mm). They are classified by the site of insertion and intended use.

Figure 1:
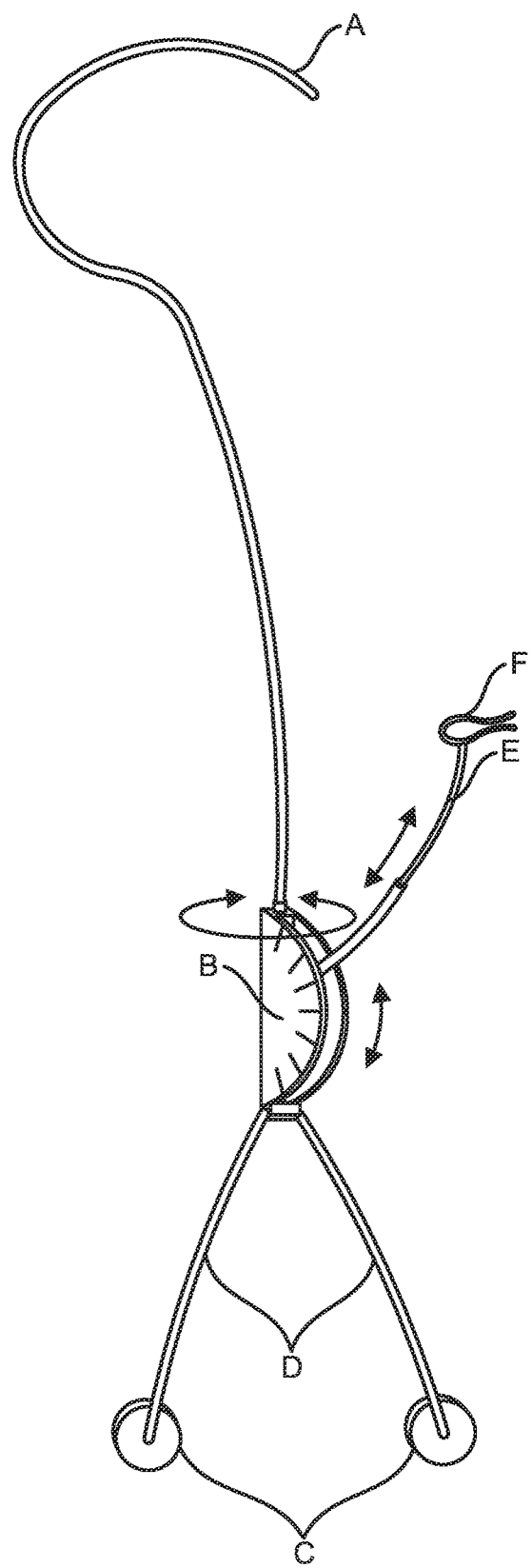
FIG. 1 depicts a gastric tube stabilizer with a rotating sideways adjustable center dial in accordance with an embodiment of the present disclosure.

Throughout the description, similar reference numbers may be used to identify similar elements depicted in multiple embodiments. Although specific embodiments of the invention have been described and illustrated, the invention is not to be limited to the specific forms or arrangements of parts so described and illustrated. The scope of the invention is to be defined by the claims appended hereto and their equivalents.

DETAILED DESCRIPTION

Reference will now be made to exemplary embodiments illustrated in the drawings and specific language will be used herein to describe the same. It will nevertheless be understood that no limitation of the scope of the disclosure is thereby intended. Alterations and further modifications of the inventive features illustrated herein and additional applications of the principles of the inventions as illustrated herein, which would occur to one skilled in the relevant art and having possession of this disclosure, are to be considered within the scope of the invention.

Throughout the present disclosure the term 'break-away' refers to an arm that has the elasticity to deform so to escape from a position around a patient's neck and yet return to its original shape to hold the prior position over and over again. The term 'universal' refers throughout the present disclosure to a joint which can move in all directions to direct and hold a feeding tube against the human body.

The present invention is a gastric tube stabilizer to stabilize tubes against the body of the patient to facilitate ease of cleaning, feeding, dispensing medication, etc.

FIG. 1 depicts a gastric tube stabilizer with a rotating sideways adjustable center dial in accordance with an embodiment of the present disclosure. This device wraps around the neck via a lightweight plastic breakaway loop A for safety. The lightweight breakaway loop extends down the front body of the patient to the adjustable center dial B, which rotates up to 360 degrees left and right and 180 degrees up and down and may lock in place according to need. A retractable feeding tube holder E extends from the center dial B, which tube holder also ratchets 180 degrees up or down and may be locked in place according to need. An interchangeable feeding tube clip F attaches to the end of the feeding tube holder E. Various tube sizes including IE B and C tube sizes are supported. Two additional support arms D extend from the lower end of the center dial B, each with a support pad C at the end.

Figure 2:
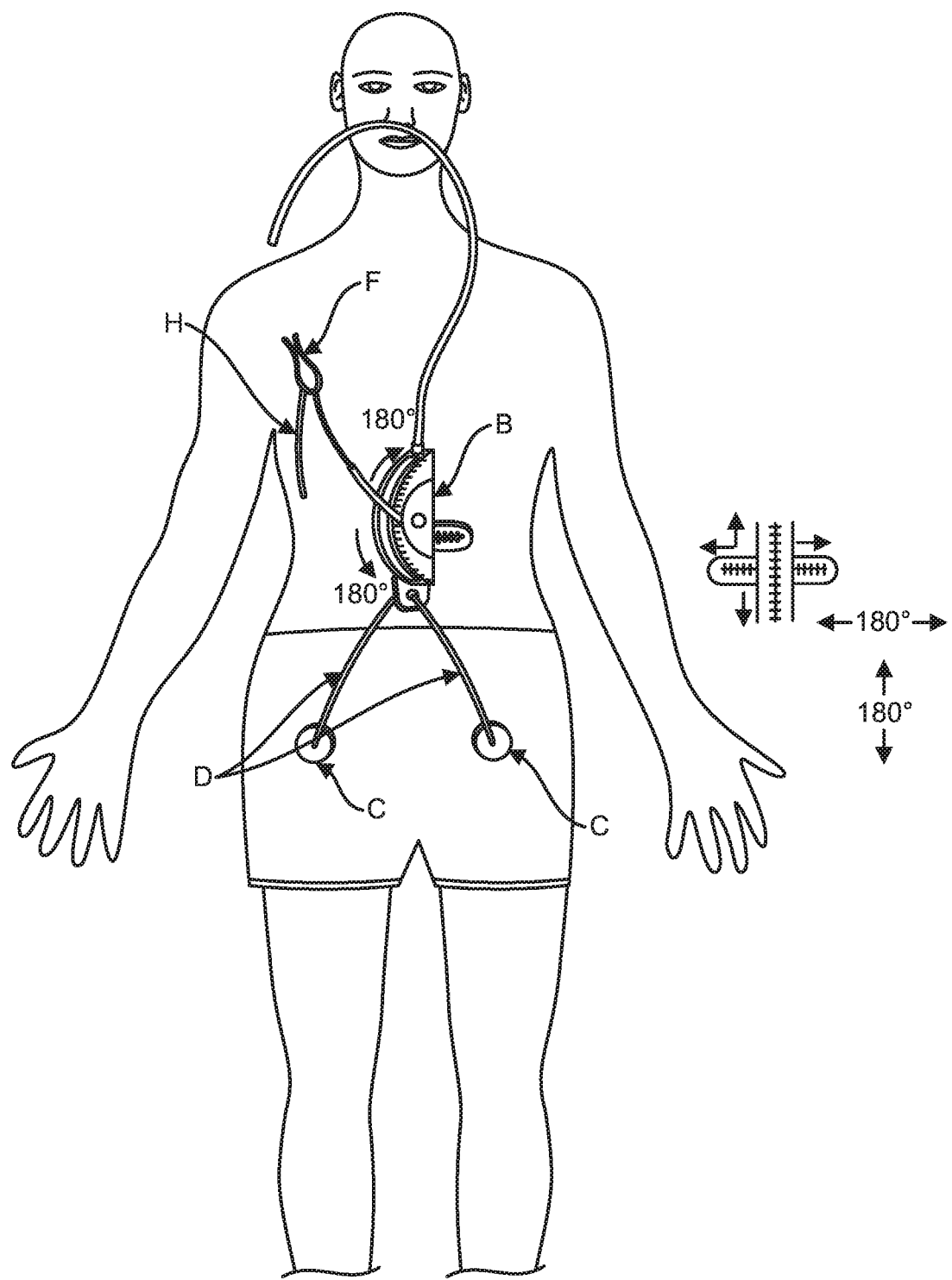
FIG. 2 depicts a gastric tube stabilizer with a rotating center adjustable center dial in accordance with an embodiment of the present disclosure.

FIG. 2 depicts a gastric tube stabilizer with a rotating center adjustable center dial against a patient's body in accordance with an embodiment of the present disclosure. This device wraps around the neck via a lightweight plastic breakaway loop A for safety. The lightweight plastic loop A extends down the front body of the patient to the adjustable center dial B, which rotates up to 360 degrees left and right and may ratchet in place according to need. A retractable feeding tube holder E extends from the center of the center dial, which tube holder E may rotate up to 360 degrees and may be locked in place as needed. An interchangeable feeding tube clip F attaches to the end of the feeding tube holder. Two additional support arms D extend from the lower end of the center dial B, each with a support pad C at the end thereof. The feeding tube H is surgically placed in the patient's chest or abdomen to extend a distance thereof for access.

Figure 3:
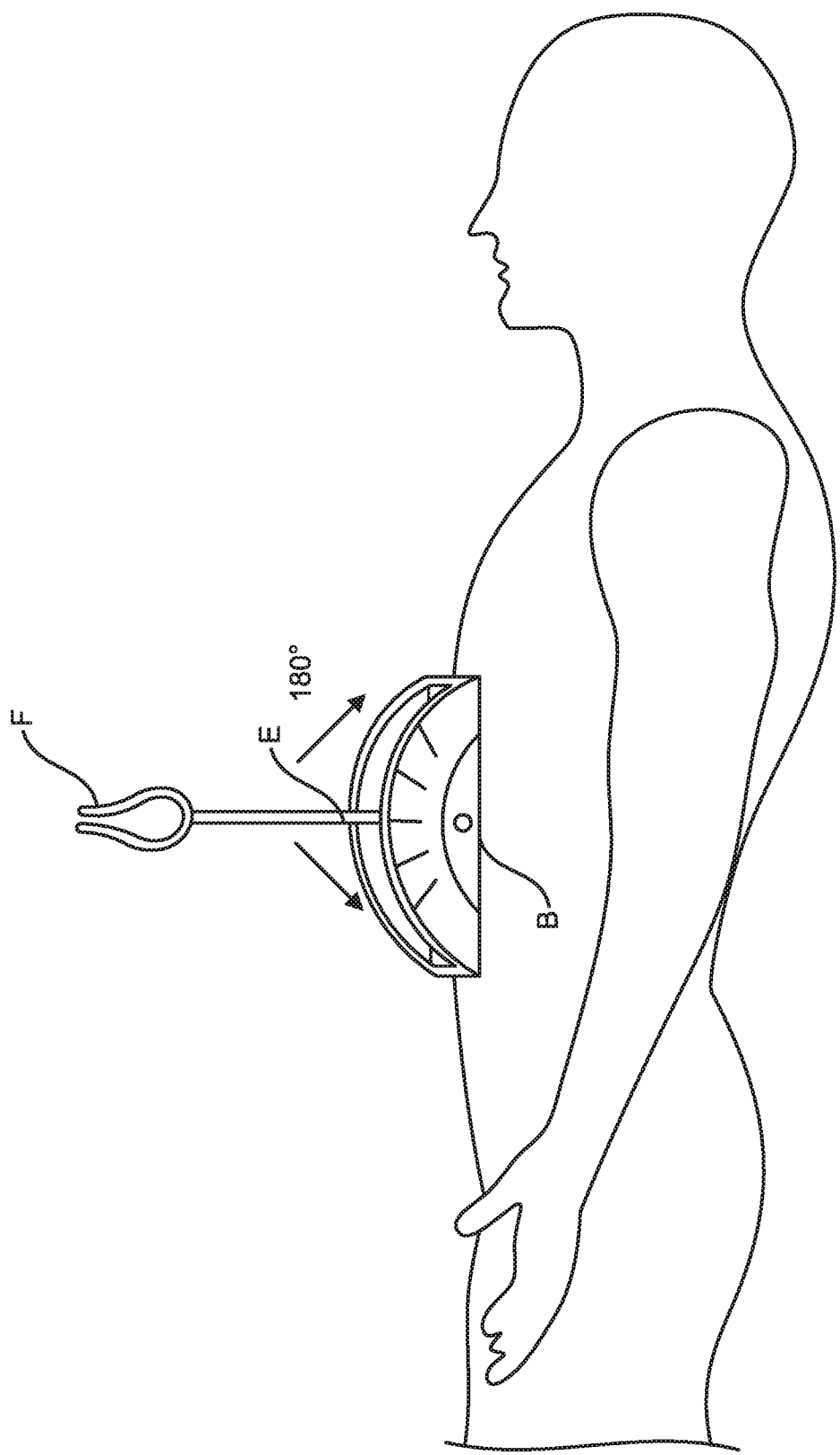
FIG. 3 is a side depiction of the device on the patient's body in accordance with an embodiment of the present disclosure.

FIG. 3 is a side depiction of the device on the patient's body in accordance with an embodiment of the present disclosure. The depiction includes limitations and reference letters and reference lines similar to other drawings explained herein. The present depiction emphasizes the device's ability to accommodate and hold a feeding tube for convenient and reliable access.

Figure 4:
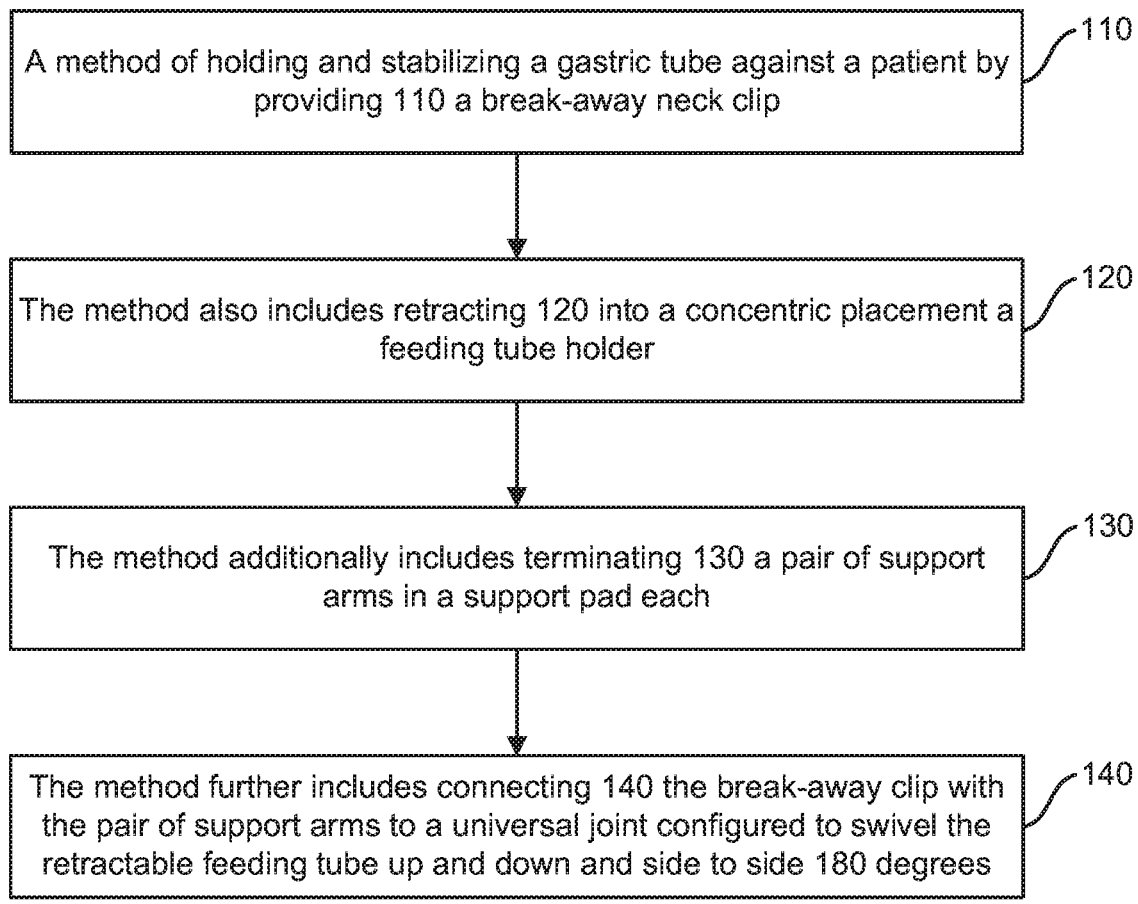
FIG. 4 depicts a flow chart of a method for stabilizing a gastric tube on a patient in accordance with an embodiment of the present disclosure.

FIG. 4 depicts a flow chart of a method for stabilizing a gastric tube on a patient in accordance with an embodiment of the present disclosure. The method for stabilizing a tube worn by a patient includes providing 110 a break-away neck clip, retracting 120 into place a feeding tube holder, terminating 130 a pair of support arms in a support pad each and connecting 140 the break-away clip with the pair of support arms to a universal joint configured to swivel the retractable feeding tube up and down and side to side 180 degrees.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The exemplary embodiment was chosen and described in order to best explain the principles of the invention and its practical application, to thereby enable others skilled in the art to best utilize the invention and various embodiments with various modifications as are suited to the particular use contemplated.

What is claimed is:

1. A tube stabilizing device worn by a patient, comprising:
   a) a break-away neck clip;
   b) a retractable feeding tube holder;
   c) a pair of support arms terminating in a support pad each; and
   d) a universal joint connecting the break-away clip with the pair of support arms and configured to swivel the retractable feeding tube up and down and side to side 180 degrees.

2. The device of claim 1, wherein the retractable feeding tube holder is retractable concentrically.

3. The device of claim 1, wherein the break-away neck clip comprises a material with a shape memory for a girth of the patient's neck.

4. The device of claim 1, wherein the pair of support arms comprise semi-rigid flex tubing.

5. The device of claim 1, wherein the support pads lay flat against the body.

6. The device of claim 1, wherein the interchangeable feeding tube holder is an interchangeable clip of various sizes to hold various feeding tube sizes.

7. The device of claim 1, wherein the universal joint is a half disc and the break-away neck clip, the pair of support arms and the retractable feeding holder attach radially thereto.

8. The device of claim 1, wherein the retractable feeding tube holder swivels up and down 180 degrees via a centric pivot in the universal joint.

9. The device of claim 1, wherein the universal joint is a half disc and swivels left to right 180 degrees via pivoting between the break-away neck clip and the pair of support arms.

10. The device of claim 1, wherein the universal joint is ratcheted into incremental radial movements.

11. A method for stabilizing a tube worn by a patient, the method comprising:
   a) providing a break-away neck clip;
   b) retracting a feeding tube holder;
   c) terminating a pair of support arms in a support pad each; and
   d) connecting the break-away clip with the pair of support arms to a universal joint configured to swivel the retractable feeding tube up and down and side to side 180 degrees.

12. The method of claim 11, further comprising concentrically retracting the retractable feeding tube holder.

13. The method of claim 11, further comprising forming the break-away neck clip from a material with a shape memory for a girth of the patient's neck.

14. The method of claim 11, further comprising forming the pair of support arms with a semi-rigid flex tubing.

15. The method of claim 11, further comprising laying the support pads flat against the body.

16. The method of claim 11, further comprising interchanging the feeding tube holder with a clip of a variable size to hold various feeding tube sizes.

17. The method of claim 11, further comprising radially attaching the break-away neck clip, the pair of support arms and the retractable feeding holder to the universal joint in a half disk configuration.

18. The method of claim 11, further comprising swiveling the retractable feeding tube holder up and down 180 degrees via a centric pivot in the universal joint.

19. The device of claim 11, further comprising swiveling the universal joint in a half disc configuration left to right 180 degrees via pivoting between the break-away neck clip and the pair of support arms.

20. The method of claim 1, further comprising ratcheting the universal joint via incremental radial movements.

* * * * *